(12) United States Patent
Ossmann et al.

(10) Patent No.: US 7,103,400 B2
(45) Date of Patent: Sep. 5, 2006

(54) ARTIFACT ELIMINATION IN TIME-GATED ANATOMICAL IMAGING

(75) Inventors: William J. Ossmann, Acton, MA (US); McKee Dunn Poland, Andover, MA (US); Xiang-Ning Li, Mill Creek, WA (US); Olivier Gerard, Viroflay (FR)

(73) Assignee: Koninklijke Philips Electronics, N.V., Eindhoven (NL)

( * ) Notice: Subject to any disclaimer, the term of this patent is extended or adjusted under 35 U.S.C. 154(b) by 386 days.

(21) Appl. No.: 10/291,060

(22) Filed: Nov. 8, 2002

(65) Prior Publication Data
US 2004/0092816 A1   May 13, 2004

(51) Int. Cl.
  *A61B 5/05*  (2006.01)
(52) U.S. Cl. .................. 600/428; 600/407; 600/413; 600/437
(58) Field of Classification Search ......... 600/407–482
  See application file for complete search history.

(56) References Cited

U.S. PATENT DOCUMENTS

| | | | |
|---|---|---|---|
| 4,800,889 A * | 1/1989 | Dumoulin et al. ......... 600/413 |
| 5,229,933 A | 7/1993 | Larson, III |
| 5,435,303 A * | 7/1995 | Bernstein et al. .......... 600/413 |
| 5,545,992 A * | 8/1996 | Foo ............................ 324/309 |
| 5,590,658 A | 1/1997 | Chiang et al. |
| 5,617,863 A | 4/1997 | Roundhill et al. |
| 5,678,552 A | 10/1997 | Savord |
| 5,800,354 A | 9/1998 | Hofland et al. |
| 5,980,458 A | 11/1999 | Clark |
| 5,993,390 A | 11/1999 | Savord et al. |
| 5,997,479 A | 12/1999 | Savord et al. |
| 6,013,032 A | 1/2000 | Savord |
| 6,126,602 A | 10/2000 | Savord et al. |
| 6,224,552 B1 | 5/2001 | Jago et al. |
| 6,292,684 B1 * | 9/2001 | Du et al. ................... 600/410 |
| 6,381,197 B1 | 4/2002 | Savord et al. |
| 6,393,313 B1 * | 5/2002 | Foo ............................ 600/410 |
| 6,771,999 B1 * | 8/2004 | Salla et al. ................ 600/413 |
| 2003/0007593 A1 * | 1/2003 | Heuscher et al. ............. 378/4 |

* cited by examiner

*Primary Examiner*—Brian L. Casler
*Assistant Examiner*—William Jung

(57) ABSTRACT

A method for anatomical imaging includes acquiring image data representative of three-dimensional volume segments of an image volume of interest in a subject. The image data are acquired in synchronism with corresponding physiological cycles of the subject. Each volume segment contains image data distributed in three dimensions. Acquiring image data includes selecting a sequence of scan lines for each respective volume segment configured to minimize an occurrence of motion artifacts throughout the image volume. The image data representative of the volume segments is combined to produce a representation of a three-dimensional anatomical image of the image volume.

31 Claims, 13 Drawing Sheets

FIGURE 2

|     | 158 |     |     |     | 160 |     |     |     | 162 |     |     |     | 164 |     |     |
| --- | --- | --- | --- | --- | --- | --- | --- | --- | --- | --- | --- | --- | --- | --- | --- |
| VS1 60 | VS1 61 | VS1 62 | VS1 63 | VS2 63 | VS2 62 | VS2 61 | VS2 60 | VS3 60 | VS3 61 | VS3 62 | VS3 63 | VS4 63 | VS4 62 | VS4 61 | VS4 60 |
| VS1 56 | VS1 57 | VS1 58 | VS1 59 | VS2 59 | VS2 58 | VS2 57 | VS2 56 | VS3 56 | VS3 57 | VS3 58 | VS3 59 | VS4 59 | VS4 58 | VS4 57 | VS4 56 |
| VS1 52 | VS1 53 | VS1 54 | VS1 55 | VS2 55 | VS2 54 | VS2 53 | VS2 52 | VS3 52 | VS3 53 | VS3 54 | VS3 55 | VS4 55 | VS4 54 | VS4 53 | VS4 52 |
| VS1 48 | VS1 49 | VS1 50 | VS1 51 | VS2 51 | VS2 50 | VS2 49 | VS2 48 | VS3 48 | VS3 49 | VS3 50 | VS3 51 | VS4 51 | VS4 50 | VS4 49 | VS4 48 |
| VS1 44 | VS1 45 | VS1 46 | VS1 47 | VS2 47 | VS2 46 | VS2 45 | VS2 44 | VS3 44 | VS3 45 | VS3 46 | VS3 47 | VS4 47 | VS4 46 | VS4 45 | VS4 44 |
| VS1 40 | VS1 41 | VS1 42 | VS1 43 | VS2 43 | VS2 42 | VS2 41 | VS2 40 | VS3 40 | VS3 41 | VS3 42 | VS3 43 | VS4 43 | VS4 42 | VS4 41 | VS4 40 |
| VS1 36 | VS1 37 | VS1 38 | VS1 39 | VS2 39 | VS2 38 | VS2 37 | VS2 36 | VS3 36 | VS3 37 | VS3 38 | VS3 39 | VS4 39 | VS4 38 | VS4 37 | VS4 36 |
| VS1 32 | VS1 33 | VS1 34 | VS1 35 | VS2 35 | VS2 34 | VS2 33 | VS2 32 | VS3 32 | VS3 33 | VS3 34 | VS3 35 | VS4 35 | VS4 34 | VS4 33 | VS4 32 |
| VS1 28 | VS1 29 | VS1 30 | VS1 31 | VS2 31 | VS2 30 | VS2 29 | VS2 28 | VS3 28 | VS3 29 | VS3 30 | VS3 31 | VS4 31 | VS4 30 | VS4 29 | VS4 28 |
| VS1 24 | VS1 25 | VS1 26 | VS1 27 | VS2 27 | VS2 26 | VS2 25 | VS2 24 | VS3 24 | VS3 25 | VS3 26 | VS3 27 | VS4 27 | VS4 26 | VS4 25 | VS4 24 |
| VS1 20 | VS1 21 | VS1 22 | VS1 23 | VS2 23 | VS2 22 | VS2 21 | VS2 20 | VS3 20 | VS3 21 | VS3 22 | VS3 23 | VS4 23 | VS4 22 | VS4 21 | VS4 20 |
| VS1 16 | VS1 17 | VS1 18 | VS1 19 | VS2 19 | VS2 18 | VS2 17 | VS2 16 | VS3 16 | VS3 17 | VS3 18 | VS3 19 | VS4 19 | VS4 18 | VS4 17 | VS4 16 |
| VS1 12 | VS1 13 | VS1 14 | VS1 15 | VS2 15 | VS2 14 | VS2 13 | VS2 12 | VS3 12 | VS3 13 | VS3 14 | VS3 15 | VS4 15 | VS4 14 | VS4 13 | VS4 12 |
| VS1 8 | VS1 9 | VS1 10 | VS1 11 | VS2 11 | VS2 10 | VS2 9 | VS2 8 | VS3 8 | VS3 9 | VS3 10 | VS3 11 | VS4 11 | VS4 10 | VS4 9 | VS4 8 |
| VS1 4 | VS1 5 | VS1 6 | VS1 7 | VS2 7 | VS2 6 | VS2 5 | VS2 4 | VS3 4 | VS3 5 | VS3 6 | VS3 7 | VS4 7 | VS4 6 | VS4 5 | VS4 4 |
| VS1 0 | VS1 1 | VS1 2 | VS1 3 | VS2 3 | VS2 2 | VS2 1 | VS2 0 | VS3 0 | VS3 1 | VS3 2 | VS3 3 | VS4 3 | VS4 2 | VS4 1 | VS4 0 |

FIGURE 10

| VS1 60 | VS2 60 | VS3 60 | VS4 60 | VS1 61 | VS2 61 | VS3 61 | VS4 61 | VS1 62 | VS2 62 | VS3 62 | VS4 62 | VS1 63 | VS2 63 | VS3 63 | VS4 63 |
|---|---|---|---|---|---|---|---|---|---|---|---|---|---|---|---|
| VS1 56 | VS2 56 | VS3 56 | VS4 56 | VS1 57 | VS2 57 | VS3 57 | VS4 57 | VS1 58 | VS2 58 | VS3 58 | VS4 58 | VS1 59 | VS2 59 | VS3 59 | VS4 59 |
| VS1 52 | VS2 52 | VS3 52 | VS4 52 | VS1 53 | VS2 53 | VS3 53 | VS4 53 | VS1 54 | VS2 54 | VS3 54 | VS4 54 | VS1 55 | VS2 55 | VS3 55 | VS4 55 |
| VS1 48 | VS2 48 | VS3 48 | VS4 48 | VS1 49 | VS2 49 | VS3 49 | VS4 49 | VS1 50 | VS2 50 | VS3 50 | VS4 50 | VS1 51 | VS2 51 | VS3 51 | VS4 51 |
| VS1 44 | VS2 44 | VS3 44 | VS4 44 | VS1 45 | VS2 45 | VS3 45 | VS4 45 | VS1 46 | VS2 46 | VS3 46 | VS4 46 | VS1 47 | VS2 47 | VS3 47 | VS4 47 |
| VS1 40 | VS2 40 | VS3 40 | VS4 40 | VS1 41 | VS2 41 | VS3 41 | VS4 41 | VS1 42 | VS2 42 | VS3 42 | VS4 42 | VS1 43 | VS2 43 | VS3 43 | VS4 43 |
| VS1 36 | VS2 36 | VS3 36 | VS4 36 | VS1 37 | VS2 37 | VS3 37 | VS4 37 | VS1 38 | VS2 38 | VS3 38 | VS4 38 | VS1 39 | VS2 39 | VS3 39 | VS4 39 |
| VS1 32 | VS2 32 | VS3 32 | VS4 32 | VS1 33 | VS2 33 | VS3 33 | VS4 33 | VS1 34 | VS2 34 | VS3 34 | VS4 34 | VS1 35 | VS2 35 | VS3 35 | VS4 35 |
| VS1 28 | VS2 28 | VS3 28 | VS4 28 | VS1 29 | VS2 29 | VS3 29 | VS4 29 | VS1 30 | VS2 30 | VS3 30 | VS4 30 | VS1 31 | VS2 31 | VS3 31 | VS4 31 |
| VS1 24 | VS2 24 | VS3 24 | VS4 24 | VS1 25 | VS2 25 | VS3 25 | VS4 25 | VS1 26 | VS2 26 | VS3 26 | VS4 26 | VS1 27 | VS2 27 | VS3 27 | VS4 27 |
| VS1 20 | VS2 20 | VS3 20 | VS4 20 | VS1 21 | VS2 21 | VS3 21 | VS4 21 | VS1 22 | VS2 22 | VS3 22 | VS4 22 | VS1 23 | VS2 23 | VS3 23 | VS4 23 |
| VS1 16 | VS2 16 | VS3 16 | VS4 16 | VS1 17 | VS2 17 | VS3 17 | VS4 17 | VS1 18 | VS2 18 | VS3 18 | VS4 18 | VS1 19 | VS2 19 | VS3 19 | VS4 19 |
| VS1 12 | VS2 12 | VS3 12 | VS4 12 | VS1 13 | VS2 13 | VS3 13 | VS4 13 | VS1 14 | VS2 14 | VS3 14 | VS4 14 | VS1 15 | VS2 15 | VS3 15 | VS4 15 |
| VS1 8 | VS2 8 | VS3 8 | VS4 8 | VS1 9 | VS2 9 | VS3 9 | VS4 9 | VS1 10 | VS2 10 | VS3 10 | VS4 10 | VS1 11 | VS2 11 | VS3 11 | VS4 11 |
| VS1 4 | VS2 4 | VS3 4 | VS4 4 | VS1 5 | VS2 5 | VS3 5 | VS4 5 | VS1 6 | VS2 6 | VS3 6 | VS4 6 | VS1 7 | VS2 7 | VS3 7 | VS4 7 |
| VS1 0 | VS2 0 | VS3 0 | VS4 0 | VS1 1 | VS2 1 | VS3 1 | VS4 1 | VS1 2 | VS2 2 | VS3 2 | VS4 2 | VS1 3 | VS2 3 | VS3 3 | VS4 3 |

| VS3 56 | VS4 56 | VS3 57 | VS4 57 | VS3 58 | VS4 58 | VS3 59 | VS4 59 | VS3 60 | VS4 60 | VS3 61 | VS4 61 | VS3 62 | VS4 62 | VS3 63 | VS4 63 |
|---|---|---|---|---|---|---|---|---|---|---|---|---|---|---|---|
| VS1 56 | VS2 56 | VS1 57 | VS2 57 | VS1 58 | VS2 58 | VS1 59 | VS2 59 | VS1 60 | VS2 60 | VS1 61 | VS2 61 | VS1 62 | VS2 62 | VS1 63 | VS2 63 |
| VS3 48 | VS4 48 | VS3 49 | VS4 49 | VS3 50 | VS4 50 | VS3 51 | VS4 51 | VS3 52 | VS4 52 | VS3 53 | VS4 53 | VS3 54 | VS4 54 | VS3 55 | VS4 55 |
| VS1 48 | VS2 48 | VS1 49 | VS2 49 | VS1 50 | VS2 50 | VS1 51 | VS2 51 | VS1 52 | VS2 52 | VS1 53 | VS2 53 | VS1 54 | VS2 54 | VS1 55 | VS2 55 |
| VS3 40 | VS4 40 | VS3 41 | VS4 41 | VS3 42 | VS4 42 | VS3 43 | VS4 43 | VS3 44 | VS4 44 | VS3 45 | VS4 45 | VS3 46 | VS4 46 | VS3 47 | VS4 47 |
| VS1 40 | VS2 40 | VS1 41 | VS2 41 | VS1 42 | VS2 42 | VS1 43 | VS2 43 | VS1 44 | VS2 44 | VS1 45 | VS2 45 | VS1 46 | VS2 46 | VS1 47 | VS2 47 |
| VS3 40 | VS4 32 | VS3 33 | VS4 33 | VS3 34 | VS4 34 | VS3 35 | VS4 35 | VS3 36 | VS4 36 | VS3 37 | VS4 37 | VS3 38 | VS4 38 | VS3 39 | VS4 39 |
| VS1 32 | VS2 32 | VS1 33 | VS2 33 | VS1 34 | VS2 34 | VS1 35 | VS2 35 | VS1 36 | VS2 36 | VS1 37 | VS2 37 | VS1 38 | VS2 38 | VS1 39 | VS2 39 |
| VS3 24 | VS4 24 | VS3 25 | VS4 25 | VS3 26 | VS4 26 | VS3 27 | VS4 27 | VS3 28 | VS4 28 | VS3 29 | VS4 29 | VS3 30 | VS4 30 | VS3 31 | VS4 31 |
| VS1 24 | VS2 24 | VS1 25 | VS2 25 | VS1 26 | VS2 26 | VS1 27 | VS2 27 | VS1 28 | VS2 28 | VS1 29 | VS2 29 | VS1 30 | VS2 30 | VS1 31 | VS2 31 |
| VS3 16 | VS4 16 | VS3 17 | VS4 17 | VS3 18 | VS4 18 | VS3 19 | VS4 19 | VS3 20 | VS4 20 | VS3 21 | VS4 21 | VS3 22 | VS4 22 | VS3 23 | VS4 23 |
| VS1 16 | VS2 16 | VS1 17 | VS2 17 | VS1 18 | VS2 18 | VS1 19 | VS2 19 | VS1 20 | VS2 20 | VS1 21 | VS2 21 | VS1 22 | VS2 22 | VS1 23 | VS2 23 |
| VS3 8 | VS4 8 | VS3 9 | VS4 9 | VS3 10 | VS4 10 | VS3 11 | VS4 11 | VS3 12 | VS4 12 | VS3 13 | VS4 13 | VS3 14 | VS4 14 | VS3 15 | VS4 15 |
| VS1 8 | VS2 8 | VS1 9 | VS2 9 | VS1 10 | VS2 10 | VS1 11 | VS2 11 | VS1 12 | VS2 12 | VS1 13 | VS2 13 | VS1 14 | VS2 14 | VS1 15 | VS2 15 |
| VS3 0 | VS4 0 | VS3 1 | VS4 1 | VS3 2 | VS4 2 | VS3 3 | VS4 3 | VS3 4 | VS4 4 | VS3 5 | VS4 5 | VS3 6 | VS4 6 | VS3 7 | VS4 7 |
| VS1 0 | VS2 0 | VS1 1 | VS2 1 | VS1 2 | VS2 2 | VS1 3 | VS2 3 | VS1 4 | VS2 4 | VS1 5 | VS2 5 | VS1 6 | VS2 6 | VS1 7 | VS2 7 |

FIGURE 11B

ARTIFACT ELIMINATION IN TIME-GATED ANATOMICAL IMAGING

BACKGROUND

The present disclosure generally relates to medical ultrasound imaging, and, more particularly, to methods and apparatus for artifact elimination in time-gated anatomical imaging.

Imaging of internal anatomical structures by ultrasound, MRI, and CT requires sequential acquisition of data from different portions of the volume to be imaged. Often these acquisitions can be completed in a time that is short enough that anatomical motions are captured clearly or are unimportant. In other cases the acquisition time is long enough that significant anatomical motion occurs, distorting or obscuring the desired image.

When the motion is periodic in time, for example, as in a cardiac or respiratory cycle, it is common practice to split the acquisition into smaller sub-volumes, each of which is acquired in a sufficiently short time to provide a good image. These sub-volumes are time-synchronized with the same point in different cycles of the periodic motion and then, after acquisition, are combined into a single image of the desired volume. Often, especially in ultrasound imaging, multiple images of each sub-volume are obtained so as to build a moving picture of the entire volume over the time of an entire cycle of the motion.

It would be desirable to obtain the entire image using as few sub-volumes as possible because this minimizes the number of cycles of the motion, e.g. heartbeats, and therefore, the time required for data acquisition. Shorter acquisition times are easier for the patient and reduce the likelihood of artifacts due to extraneous motion of the patient or the imaging equipment or due to departures from perfect repeatability of the anatomical motion over multiple cycles.

Unfortunately, using fewer sub-volumes requires that they each be larger if they are to encompass the same volume of interest, thereby increasing the acquisition time for each sub-volume. If the anatomical motion is fast enough, the amount of motion during the acquisition time of a single sub-volume will be large enough to cause image artifacts at the boundaries between sub-volumes. For example, in volumetric imaging of the heart, data at the final edge of one subvolume would be acquired slightly later in the heartbeat than the data at the adjacent starting edge of the next sub-volume. A fast-moving portion of the heart wall crossing this boundary between sub-volumes would be shown in slightly different positions on either side of the boundary, resulting in a "tearing" artifact which will be visually objectionable and may cause difficulties in the reconstruction of the whole image.

In U.S. Pat. No. 5,993,390, a segmented 3-D cardiac ultrasound imaging apparatus builds a volumetric image of the heart by acquiring image data from several separate volume segments during separate cardiac cycles (heartbeats). The apparatus splices the images together to make a single volumetric image. The time within a cardiac cycle when the image data are acquired is referred to the cardiac phase, and an entire volume segment is imaged at the given phase in the cardiac cycle allocated to that volume segment.

However, when a fast-moving structure such as a heart valve spans a boundary between volume segments, a "tearing" artifact can sometimes occur. A probable cause may be due to the fact that even within a single cardiac phase, the time needed to acquire all of the data from a volume segment was sufficient for the fast-moving valve to be in a slightly different position in one volume segment in which it was imaged at the beginning of the phase, than in the adjacent volume segment in which it was imaged at the end of the phase. Accordingly, when the volume segment images are spliced together, the valve briefly appears "torn".

Let us consider further the case of volumetric ultrasound imaging of the heart. Due to the speed of cardiac motions, it is desirable to obtain image data at as high a frame rate as possible. Images of the entire region of interest must be obtained as frequently as possible. Typically 15 Hz frame rates are barely usable; 30–60 Hz being preferable.

The amount of time required to obtain ultrasound data from a large volume encompassing most of the heart is long enough that an adequately high frame rate may not be possible. In such a case, the practice is to acquire the data in several smaller adjacent sub-volumes, each synchronized with a different beat of the cardiac cycle via an ECG signal. Then the sub-volumes are spliced together in the displayed image as if they were all from the same cycle. As illustrated in FIG. 1, each sub-volume consists of n 2-D scan planes with the order of scanning from 1 to n noted at the bottom for the first two sub-volumes (10, 12). The scan planes are oriented perpendicular to the page and stacked left to right. In each sub-volume, after a synchronization trigger from the ECG, the scan planes are acquired in the order indicated, so that like-numbered scan planes are acquired at essentially the same instant in different cardiac cycles.

The problem comes at the boundaries between sub-volumes. At the boundaries, the scan plane acquired at the end of the frame in one sub-volume (10) is displayed adjacent to the scan plane acquired at the beginning of the frame in the next sub-volume (12). A fast-moving part of the heart such as a valve will have moved enough, even during the relatively short frame time to be in different positions at the beginning and end of the frame time. This results in the "tearing" artifact 14 depicted in FIG. 1.

As a result, a single acquisition from a volume segment has been treated as if it were acquired instantaneously, but in fact is not. A small amount of time elapses between the first line acquired and the last (between the beginning and the end of the cardiac phase). This is not a problem within a single region, since so long as adjacent scan lines were acquired close in time to each other, the tissue imaged by those lines will all be in nearly perfect relative alignment. However, stacking multiple volume segments, with typical prior art scan patterns, together can cause image artifacts at the volume segment boundaries because the end of one volume segment's acquisition is spliced to the beginning of the next volume segment's acquisition.

FIG. 2 illustrates a schematic cross-sectional view of an imaged volume perpendicular to the scan lines. The locations of individual scan lines 16 and four (4) volume segments 18, 20, 22 and 24 are shown. The scan lines are numbered in the order of their acquisition; each line is designated with the volume segment to which it belongs (VSn) and the line number within that volume segment. In this example, there are only sixteen (16) rows and four (4) columns per volume segment, but typically there would be many more lines in a volume segment. A discontinuity at the boundary can be observed in FIG. 2, as indicated by reference numeral 26, there being a difference of forty eight (48) scan lines worth of time across the boundary. With more lines in a volume segment, this difference would be higher.

Accordingly, a method and apparatus for artifact elimination in time-gated anatomical imaging which overcomes the problems in the art discussed above would be desirable.

SUMMARY

A method for anatomical imaging includes acquiring image data representative of three-dimensional volume segments of an image volume of interest in a subject. The image data is acquired in synchronism with corresponding physiological cycles of the subject. Each volume segments contains image data distributed in three dimensions. Acquiring image data includes selecting a sequence of scan lines for each respective volume segment configured to minimize an occurrence of motion artifacts throughout the image volume. The image data representative of the volume segments is combined to produce a representation of a three-dimensional anatomical image of the image volume.

BRIEF DESCRIPTION OF THE DRAWINGS

FIG. 2 is an illustrative view of known line sequencing;

FIG. 10 is an illustrative view of a line sequence with no discontinuities between volume segments according to another embodiment of the present disclosure;

FIGS. 11A and 11B are illustrative views of interleaved volume segments according to additional embodiments of the present disclosure;

DETAILED DESCRIPTION

Figure 3:
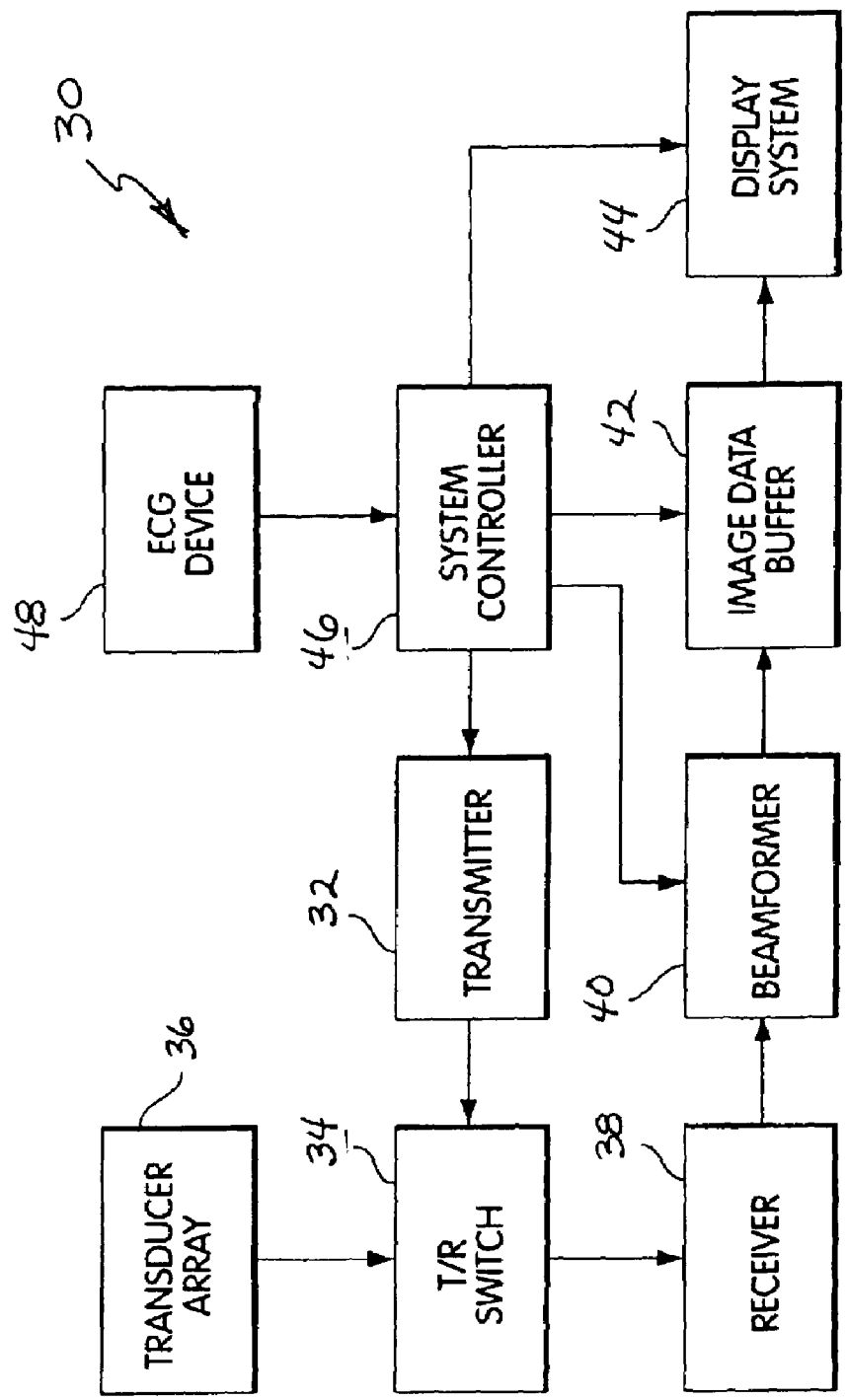
FIG. 3 is a block diagram of an example of an ultrasound imaging system suitable for implementing the present invention.

A simplified block diagram of an example of an ultrasound imaging system 30 suitable for implementing the present invention is shown in FIG. 3. An ultrasound transmitter 32 is coupled through a transmit/receive (T/R) switch 34 to a transducer array 36. Transducer array 36 may be a two-dimensional array of transducer elements for performing three-dimensional scanning. The transducer array 36 transmits ultrasound energy into a region being imaged and receives reflected ultrasound energy, or echos, from various structures and organs within the patient's body. The transmitter 32 includes a transmit beamformer. By appropriately delaying the pulses applied to each transducer element by transmitter 32, the transmitter 32 transmits a focused ultrasound beam along a desired transmit scan line.

The transducer array 36 is coupled through T/R switch 34 to an ultrasound receiver 38. Reflected ultrasound energy from a given point within the patient's body is received by the transducer elements at different times. The transducer elements convert the received ultrasound energy to received electrical signals which are amplified by receiver 38 and are supplied to a receive beamformer 40. The signals from each transducer element are individually delayed and then are summed by the beamformer 40 to provide a beamformer signal that is a representation of the reflected ultrasound energy level along a given receive scan line. As known in the art, the delays applied to the received signals may be varied during reception of ultrasound energy to effect dynamic focusing. The process is repeated for multiple scan lines to provide signals for generating an image of a region of interest in the patient's body. Because the transducer array is two-dimensional, the receive scan lines can be steered in azimuth and in elevation to form a three-dimensional scan pattern. The beamformer 40 may, for example, be a digital beamformer such as may be found in any suitable commercially available medical diagnostic ultrasound machine.

The beamformer signals are stored in an image data buffer 42 which, as described below, stores image data for different volume segments of an image volume and for different cardiac phases of a cardiac cycle. The image data is output from image data buffer 42 to a display system 44 which generates a three-dimensional image of the region of interest from the image data. The display system 44 may include a scan converter which converts sector scan signals from beamformer 40 to conventional raster scan display signals.

A system controller 46 provides overall control of the system. The system controller 46 performs timing and control functions and typically includes a microprocessor and associated memory.

An ECG device 48 includes ECG electrodes attached to a subject or patient. The ECG device 48 supplies ECG waveforms to system controller 46 for synchronizing imaging to the patient's cardiac cycle, as described in detail below.

Figure 4:
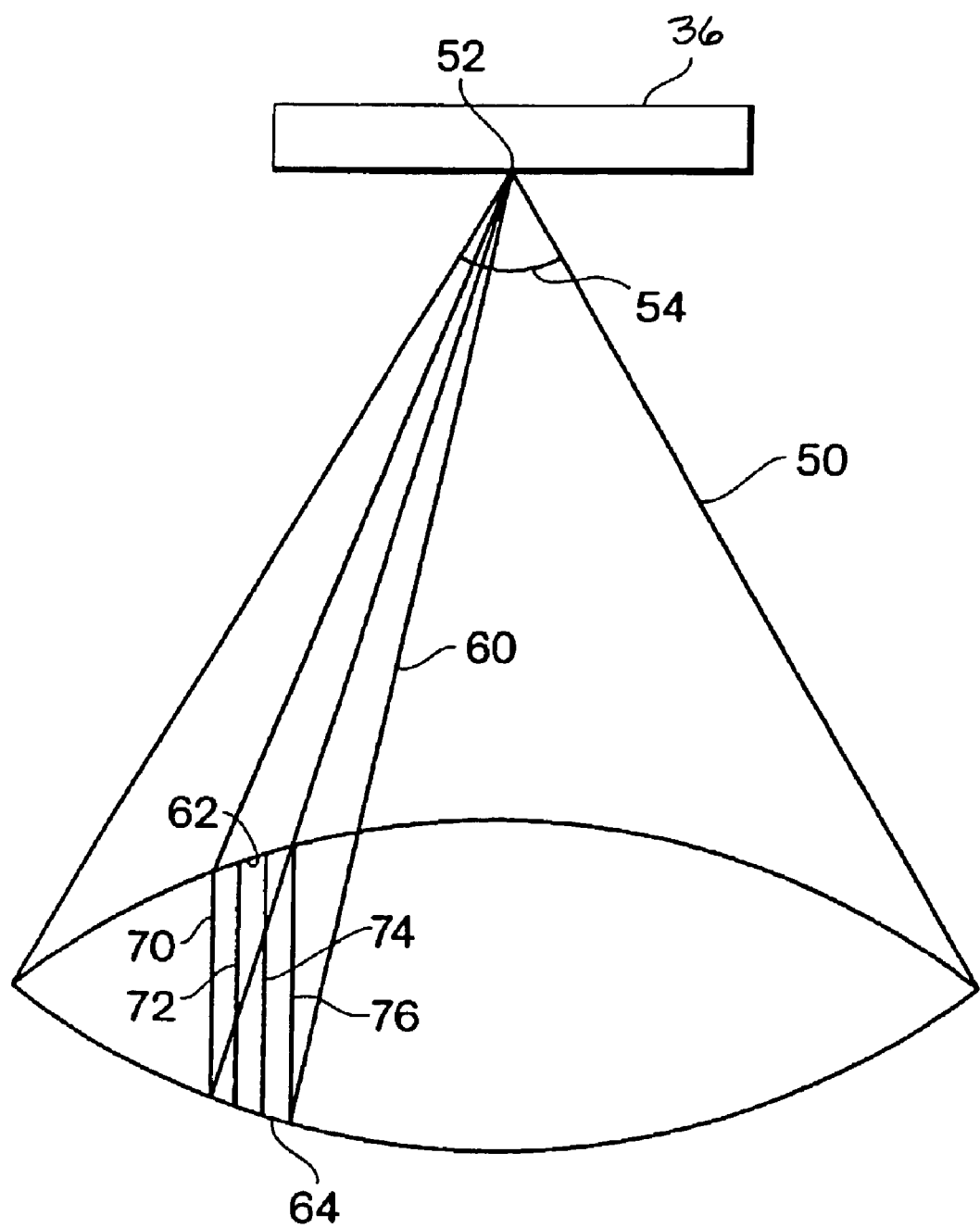
FIG. 4 is a schematic representation of a three-dimensional image volume and a volume segment of the image volume.

An example of a three-dimensional image volume 50 for which an image may be acquired in accordance with the present invention is shown in FIG. 4. Image volume 50 may have a conical shape with an apex 52 centered on transducer array 36. Image data for image volume 50 may be acquired by three-dimensional ultrasound imaging. Volume 50 may, for example, be imaged as a plurality of two-dimensional sector-shaped slices. The diameter of conical image volume 50 may be defined in terms of the required number of receive lines to achieve a desired resolution. The required number of receive lines to acquire a complete image of volume 50 is given by $\pi L^2/4$, where L is the diameter of conical image volume 50 in units of receive lines. Thus, for example, where image volume 50 has a diameter of 120 receive lines, 11,304 receive lines are needed to acquire image data for volume 50.

One embodiment of the present disclosure relates to cardiac imaging. To facilitate cardiac imaging, image volume 50 may be divided into three-dimensional volume segments for imaging of a patient's heart. An example of a volume segment is illustrated in FIG. 4.

Volume segment 60 is a three-dimensional slice of conical image volume 50 from a first side 62 to a second side 64, and may be imaged as a series of two-dimensional sector-shaped slices 70, 72, 74 and 76. The entire image volume 50 is divided into volume segments.

The volume segments which constitute image volume 50 may have any desired size and shape. Thus, for example, the cross-sections of the volume segments may be square, rectangular, circular, or irregularly shaped. Furthermore, different volume segments may have different sizes and shapes within a single image volume. In addition, the volume segments are not necessarily imaged as a series of two-dimensional slices. A sufficient number of transmit and receive lines are utilized to obtain a desired image resolution. The imaging protocol uses a desired pattern further as discussed herein. For a given image volume, the selection of the size, shape and number of volume segments may be based in part on the time available for image data acquisition during a specified cardiac phase as described below. Image data corresponding to different volume segments may be acquired with different apertures of transducer array 36.

It will be understood that the image volume itself is not limited to a conical shape and may have a variety of different shapes and sizes. For example, the image volume may be a pyramid or a truncated pyramid. The selection of the size and shape of the image volume may be based on the application and the type of transducer being utilized.

Figure 5:
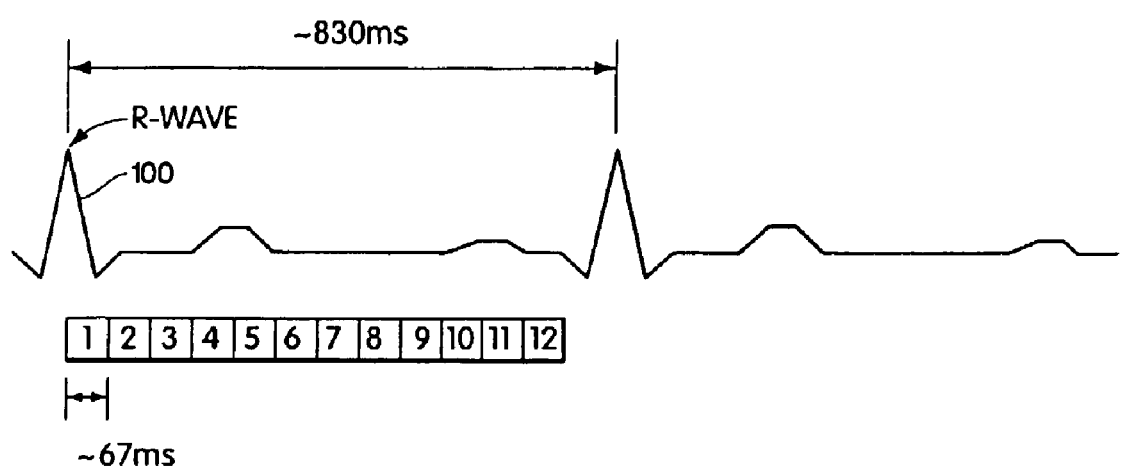
FIG. 5 shows an ECG waveform that is divided into twelve cardiac phases.

A feature of the invention is based on acquisition of image data for one or more volume segments in synchronism with the patient's cardiac cycle. An example of an ECG waveform is shown in FIG. 5. In the example of FIG. 5, ECG waveform 100 indicates a heartbeat every 830 milliseconds. The cardiac cycle may be divided into cardiac phases for imaging. In one example, 12 cardiac phases of approximately 67 milliseconds each may be utilized. The selection of the cardiac phase duration is typically based on the maximum time in which the heart does not move significantly. More or fewer cardiac phases may be utilized.

By obtaining a three-dimensional image representing the heart in each of the cardiac phases, a variety of information can be obtained. The three-dimensional images of the heart at successive cardiac phases can be displayed as a function of time to represent heart movement. The moving image can be used to identify end systole and end diastole and to perform other diagnostics. Images for a selected cardiac phase can be rotated to a desired orientation for improved analysis. Image analysis techniques can be utilized to quantify maximum and minimum volumes of the left ventricle. From this information, ejection volume and ejection fraction can be calculated.

In accordance with an aspect of the invention, image data for three-dimensional volume segments of the image volume is acquired during successive cardiac cycles until a complete image is acquired. The ECG waveform of the patient is used to trigger image data acquisition, so that data acquisition is synchronized to the patient's cardiac cycle. More specifically, image data acquisition is synchronized to a specific phase of the cardiac cycle. Furthermore, image data may be acquired during each phase of each cardiac cycle. The amount of image data acquired during each cardiac phase is a function of the duration of the cardiac phase and the speed of image data acquisition.

Referring again to the example of FIG. 4, assume that conical image volume 50 has an angle of 90 degrees (indicated by reference numeral 54) and is 16 centimeters deep. For this image volume and a sound speed of 1540 meters per second, three-dimensional image data may be acquired in 587 milliseconds. This imaging time is based on the use of parallel receive techniques in which four receive lines are processed for each transmit event. Accordingly, approximately one ninth of the image data for image volume 50 may be acquired during a cardiac phase of 67 milliseconds, and image data for a complete three-dimensional image of the image volume is acquired in nine heartbeats. Image data for a volume segment may be acquired during one or more cardiac phases of a single cardiac cycle. That is, image data acquisition for a specified volume segment may be repeated during each cardiac phase. Thus, in nine heartbeats a complete three-dimensional image may be acquired for each of the 12 cardiac phases, for a total of 12 three-dimensional images. The image data may be stored in image data buffer 42 (FIG. 3) and combined into images following data acquisition. The total acquisition time in this example is 7.5 seconds, thereby minimizing motion problems and allowing image data to be acquired in one breathold.

Figure 6:
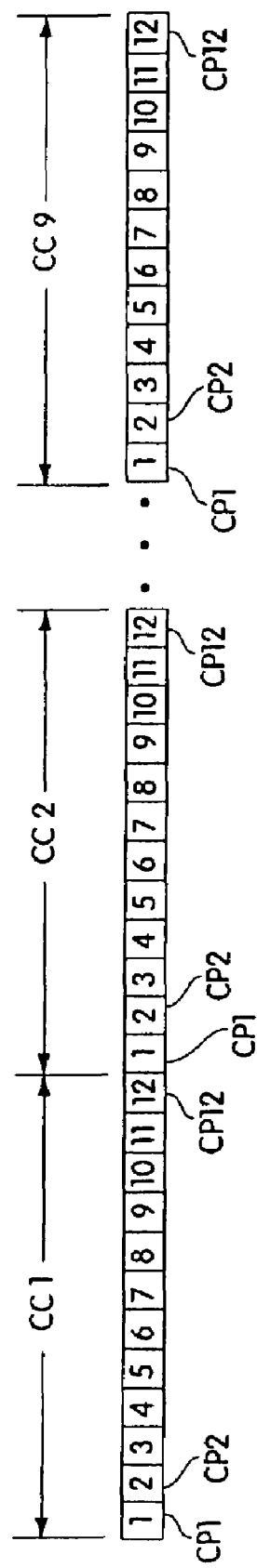
FIG. 6 shows an example of an ECG waveform wherein a three-dimensional image is acquired in nine heartbeats.

The acquisition of the image data for the nine volume segments which constitute the image volume is described with reference to FIGS. 5 and 6. The image volume is defined as having volume segments VS1–VS9. Each cardiac cycle is defined as having cardiac phases CP1–CP12. Image data is acquired during cardiac cycles CC1–CC9. Using this notation, image data for volume segment VS1 is acquired during cardiac phase CP1 of cardiac cycle CC1. Image data acquisition for volume segment VS1 is repeated during cardiac phases CP2–CP12 of cardiac cycle CC1. Image data for volume segment VS2 is similarly acquired during each of cardiac phases CP1–CP12 of cardiac cycle CC2. The same approach is used for cardiac cycle CC3–CC9, so that image data for volume segment VS9 is acquired during each of cardiac phases CP1–CP12 of cardiac cycle CC9. All of the image data are stored in image data buffer 42.

The image data stored in image data buffer 42 are organized and combined to form a three-dimensional image of the image volume in each cardiac phase. Thus, image data for volume segments VS1 through VS9, acquired during cardiac phase CP1 of cardiac cycles CC1–CC9, are combined to provide a three-dimensional image of cardiac phase CP1. Similarly, image data for volume segments VS1 through VS9, acquired during cardiac phase CP2 of cardiac cycles CC1–CC9, are combined to provide a three-dimensional image of cardiac phase 2. The same approach is used for cardiac phases CP3–CP12. Thus, 12 three-dimensional images of the 12 cardiac phases are obtained in nine heartbeats.

As indicated above, the image volume may be divided into a different number of volume segments. Furthermore, the cardiac cycle may be divided into a different number of cardiac phases. Image data for a single larger volume segment or for two or more smaller volume segments may be acquired during a cardiac cycle. The selection of these parameters depends on a number of factors, including the desired resolution, the imaging speed, i.e., the time to acquire a complete three-dimensional image, and the size of the image volume.

Figure 7:
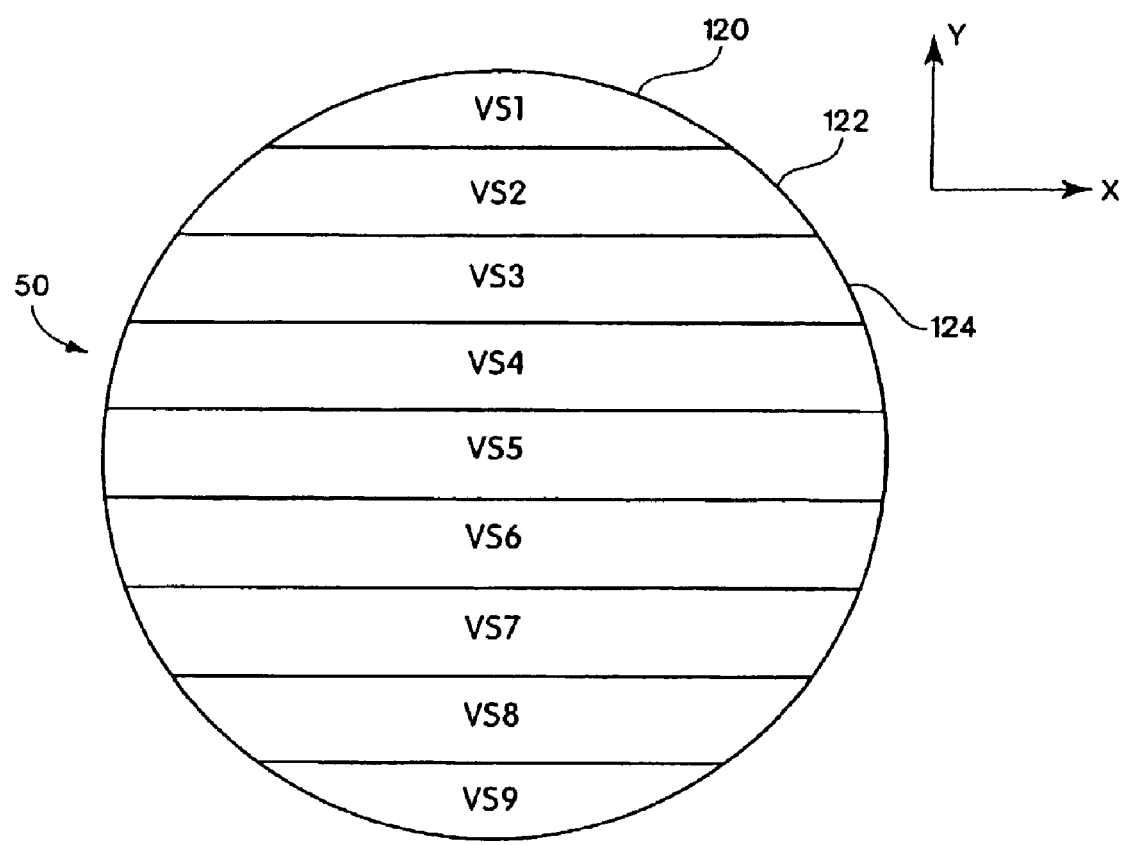
FIG. 7 is a cross-sectional view of a three-dimensional image volume that is divided into abutting volume segments.

Different imaging protocols may be used to acquire volume segment image data. An example of an imaging protocol using abutting volume segments is shown in FIG. 7. A cross section of conical image volume 50 is shown. Volume segments 120, 122, 124, etc. comprise abutting, three-dimensional slices of the conical image volume. Each of the volume segments 120, 122, 124, etc. may be imaged as a series of two-dimensional sector-shaped slices. Nine volume segments constitute the image volume 50 in this example. The volume segments may be imaged in any desired order. In one embodiment, abutting volume segments are imaged in succession, i.e., volume segment 120, followed by volume segment 122, followed by volume segment 124, etc. By imaging abutting segments in succession, adjacent image data are acquired from either the same cardiac cycle or consecutive cardiac cycles. Thus, discontinuities in the image data are minimized. In the imaging protocol of FIG. 7, a high resolution, three-dimensional image of the image volume is available after nine heartbeats.

Some images of anatomy undergoing repetitive motion, for example, the heart, are produced by combining images of smaller sub-volumes acquired at different times in synchrony with the repetition. The method and apparatus of the present disclosure are configured to substantially eliminate motion artifacts in such images. According to one embodiment, the method and apparatus accomplish this by arranging the data acquisition within time-gated sub-volumes in a manner so that data near the boundaries of one sub-volume are taken at the same time relative to the repetition as nearby data in adjacent sub-volumes, eliminating the difference in position of anatomical structures across the boundary.

In another embodiment, an imaging apparatus provides a means of gathering time-gated image data from physically adjacent parts of an anatomical structure at the same relative time in the repetitive anatomical cycle (heartbeat), even though the data may have been acquired during different cycles. This ensures that the adjacent parts will be imaged in adjacent positions rather than physically separated positions as could occur if they were imaged at different relative times in the cycle.

Accordingly, the imaging method and apparatus of the present disclosure substantially eliminate tearing artifacts in a reconstructed 3-D image, thereby allowing acquisition in fewer heartbeats and less time than might otherwise be possible. Since less image acquisition time is required, there is less possibility of other artifacts due to motion of the equipment or irregular repetitions of the anatomical cycle. In cases where breath motion artifacts are compounded with the cardiac cycle, shorter imaging times may also allow elimination of gating the data acquisition on respiratory action in favor of a short breath hold by the patient. In situations where blood flow is being imaged, the method and apparatus of the present disclosure substantially eliminates discontinuities in the rendition of the flow information.

Figure 8:
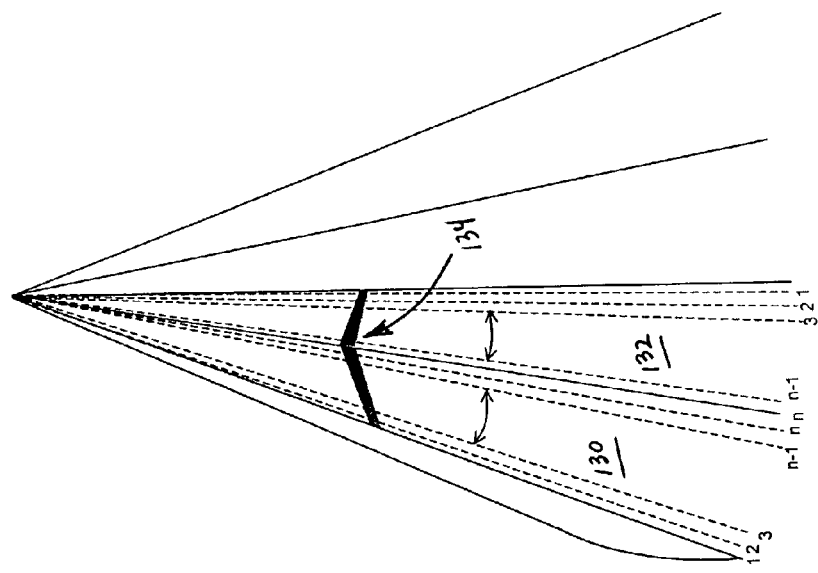
FIG. 8 is an illustrative view of scan line sequencing resulting in a substantial artifact elimination at a volume segment boundary according to an embodiment of the present disclosure.
Figure 1:
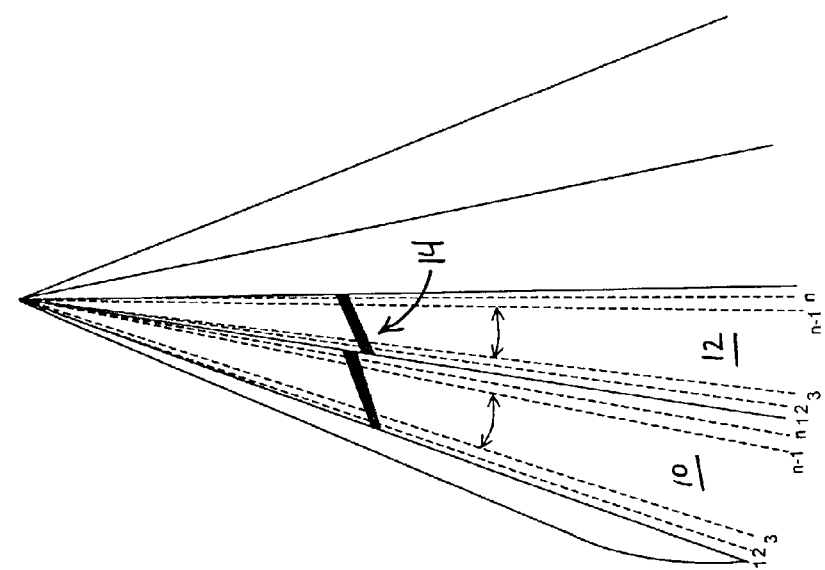
FIG. 1 is an illustrative view of scan line sequencing resulting in tearing at a volume segment boundary.

The method and apparatus of the present disclosures utilize a sequence of data acquisition in anatomical imaging that reduces certain kinds of image artifacts. For example, according to one embodiment, the method and apparatus are configured to reverse the order of scan plane acquisition (1, 2, 3, . . . , n−1, n) in every other sub-volume, as shown in FIG. 8. As shown, the scan plane acquisition order for subvolume 130 is the reverse of the scan plane acquisition order of neighboring subvolume 132. Accordingly, scan planes adjacent to sub-volume boundaries will be acquired at the same time within a frame as their neighbors across the boundaries. The result is that anatomical structures appear continuous across the boundaries. The "tearing" artifact, such as indicated by reference numeral 14 and shown and described in connection with FIG. 1, has been reduced to a shape distortion as indicated by reference numeral 134 of FIG. 8. Other scan orders, for example, from the center of a sub-volume outward could also be used.

Figure 9:
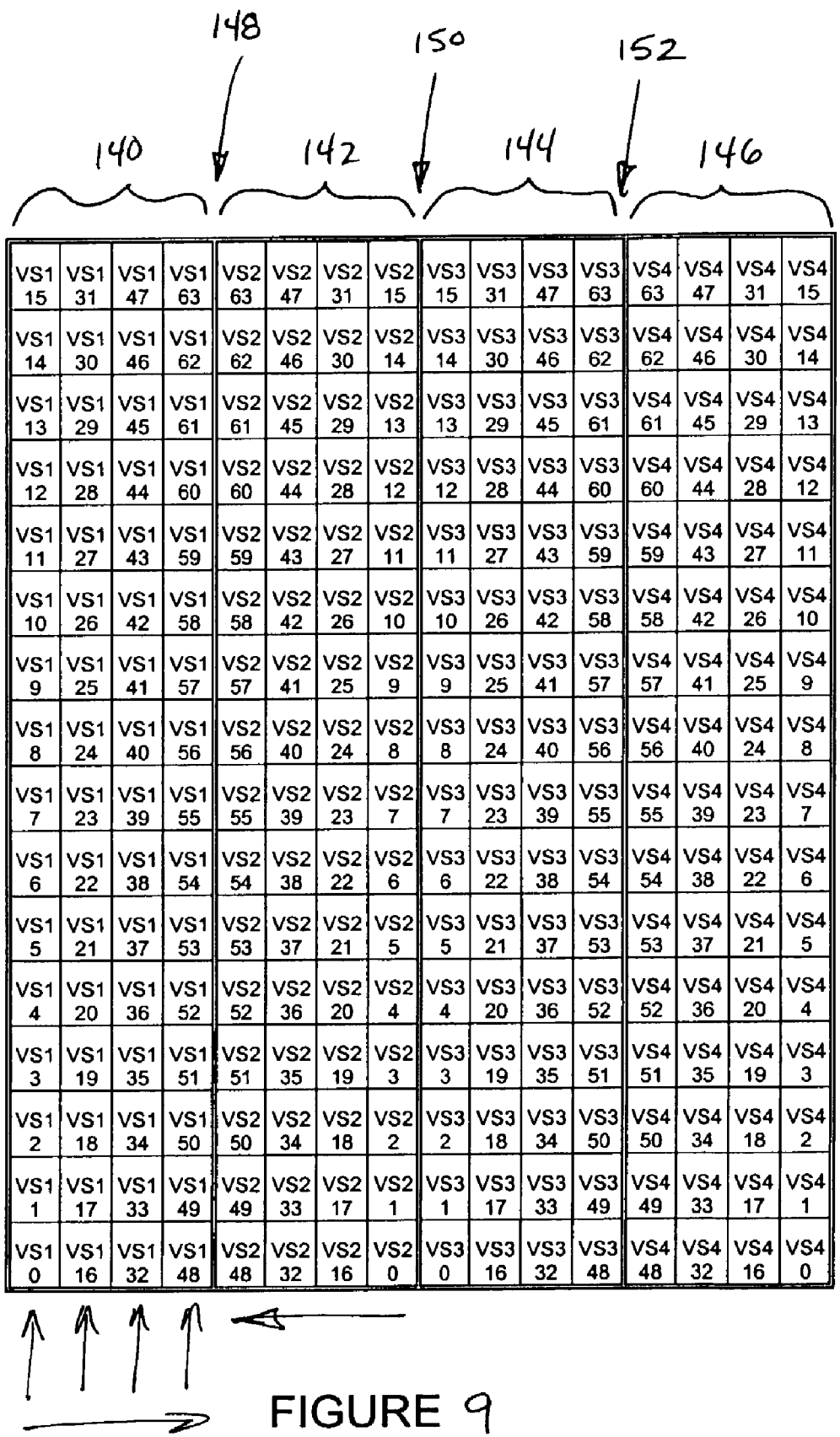
FIG. 9 is an illustrative view of the line sequencing of FIG. 8 with no discontinuities between volume segments according to an embodiment of the present disclosure.

FIG. 9 is an illustrative view of the line sequencing of FIG. 8 with no discontinuities between volume segments. In FIG. 9, the order of the scan planes in alternate volume segments, such as alternate volume segments (140, 142), (142, 144), (144, 146), and (146, 148), is reversed. Discontinuity at the respective volume segment boundary (148, 150, and 152, respectively) is removed. This pattern can be continued for as many volume segments as desired. Other patterns of line acquisition can be configured to achieve similar results. For example, the scan planes may be acquired starting at the center of each volume segment and working outward on alternating sides of the volume segment, or equivalently starting at the boundaries and working inward.

While described herein with reference to several particular scanning configurations, the method and apparatus can be extended to other patterns and possibly even other imaging modalities in which time synchronization with the cardiac, or other, cycles is used to assemble sequentially acquired data into a single image. A feature of the method and apparatus of the present embodiments is that the order of data acquisition is selected so as to eliminate image discontinuities at the boundaries between sub-images. In addition, as discussed herein, several methods of disposing the individual lines within a volume segment are configured so as to eliminate the time discontinuity across the volume segment boundaries. Still further, some of the methods are configured to reduce the local time gradient throughout the volume (but not the total time) of the a volume segment, accordingly reducing an image distortion within a given subvolume and between adjacent sub-volumes.

In another embodiment, a scan pattern is configured as shown in FIG. 10. As shown in FIG. 10, the direction 154 of the scan planes within a subvolume is rotated 90 degrees from the direction between adjacent subvolumes (158, 160, 162, and 164). In adjacent volume segments, the scan order is mirror-imaged so as to eliminate any discontinuity across the respective volume segment boundary between adjacent volume segments. Since the volume segments in this embodiment are narrower than they are wide, this pattern has the added advantage of reducing the maximum amount of time between adjacent scan lines in the same volume segment, thus reducing distortion and artifacts within the individual volume segments. Still further, acquiring image data can include configuring individual scan lines of a sequence to reduce a local time gradient throughout the volume segment to less than ten percent (10%) of a total time for acquiring image data for each volume segment.

Figure 2:
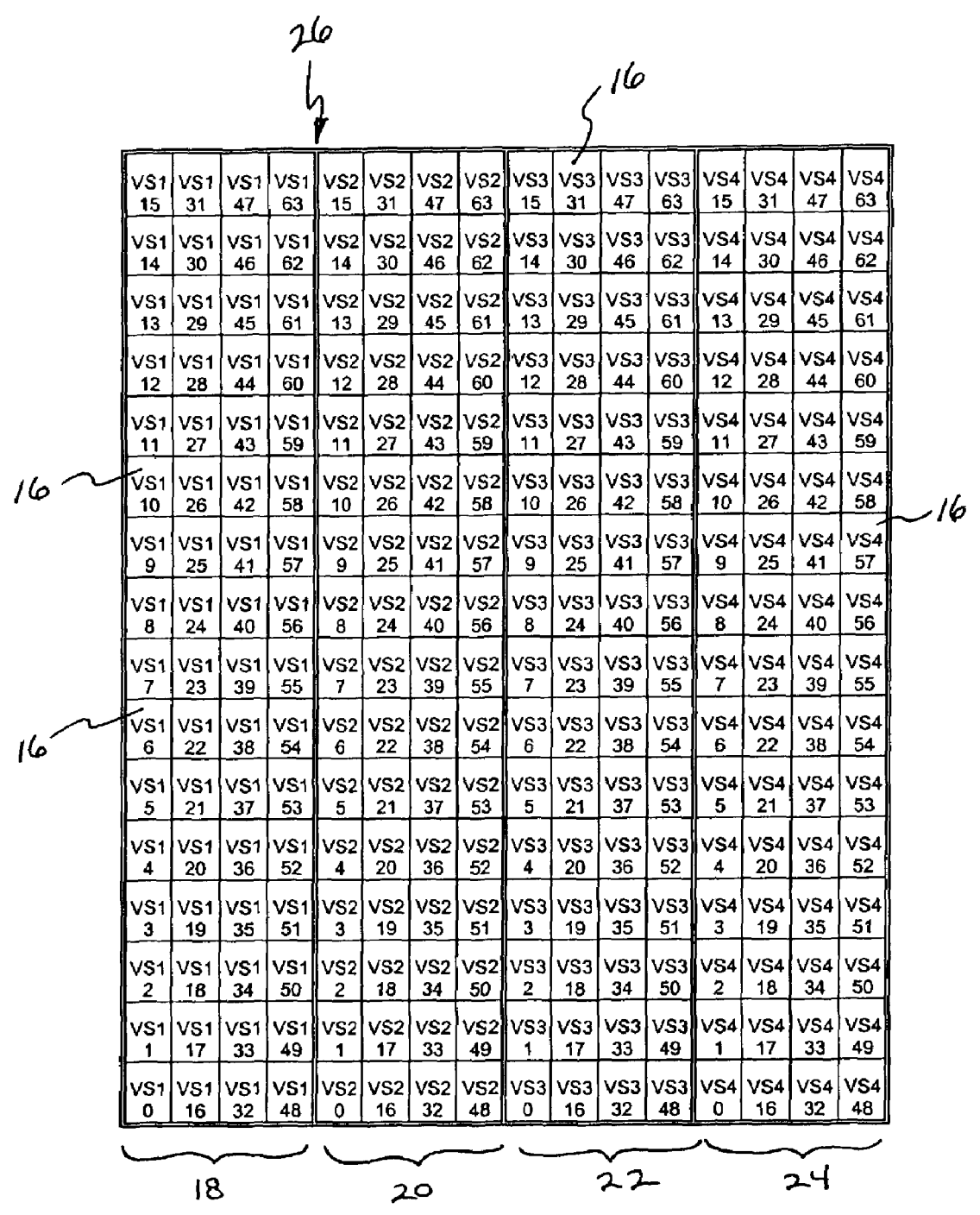

According to yet another embodiment, the volume segments need not be simply connected in the geometric sense. Any or all of the volume segments (VS1, VS2, VS3, and VS4) could consist of multiple smaller portions that need not be connected to each other. In this embodiment, the scan order is configured to meet the requirement that differences in acquisition times across all volume segment boundaries be minimized. FIG. 11A shows an example of this embodiment in which the volume segments (VS1, VS2, VS3, and VS4) are disposed as interleaved planes and ordered such that most of the boundaries show no discontinuity, and across those boundaries that do have a discontinuity, it is only one forty-eighth of the amount which occurs between adjacent planes within an individual volume segment of the prior art scan pattern (FIG. 2). Not only does this embodiment reduce time discontinuities between adjacent lines, but the overall pattern shows a high correlation of line times within any given region of the scanned volume, whether the particular region spans multiple volume segments or not. Accordingly, this embodiment minimizes distortion in the final image due to movement of the heart, since all parts of the heart are imaged at almost exactly the same time within the cardiac phase as nearby parts.

As shown in FIG. 11B, volume segments VS1, VS2, VS3, and VS4 are interleaved in two dimensions. That is, neighboring lines in first and second directions are in different volume segment. Note that the volume segments of FIG. 11A are interleaved in one direction. That is, the neighbors of each line are in the same volume segment in one direction but in different volume segments in the other direction.

In connection with performing 3D imaging according to the embodiments of the present disclosure, the method includes use of parallel processing. With parallel processing, multiple lines of an image are required simultaneously. In one embodiment, the lines are generally adjacent to each other, however, there is no intrinsic need for the same. This differs from a strict sequential ordering and amounts to a sequential ordering of simultaneous groups of lines.

Accordingly, different techniques may be used for acquiring image data within each of the volume segments. In one example, each volume segment includes a plurality of two-dimensional slices. The sequence for obtaining image data for each of the receive lines within the volume segment utilizes a sequence of scan lines for each respective volume segment configured to minimize an occurrence of motion artifacts throughout the image volume. The selected sequence is also configured to be compatible with the technique used for providing delay data to the receive beamformer.

According to another embodiment of the present disclosure, a method for anatomical imaging, comprises: a) acquiring image data representative of three-dimensional volume segments of an image volume of interest in a subject, in synchronism with corresponding physiological cycles of the subject, each of the volume segments containing image data distributed in three dimensions, wherein acquiring image data includes selecting a sequence of scan lines for each respective volume segment configured to minimize an occurrence of motion artifacts throughout the image volume; and b) combining the image data representative of the volume segments to produce a representation of a three-dimensional anatomical image of the image volume. The method further includes repeating the acquiring and combining to generate a sequence of images and forming a time history of images or a motion picture of images. In addition, acquiring image data further includes configuring the sequence of scan lines within each respective volume segment to minimize time discontinuities within each volume segment, as well as minimizing time discontinuities across adjacent volume segment boundaries.

Acquiring image data can include selecting the sequence of scan lines within each respective volume segment to minimize the occurrence of motion artifacts across adjacent volume segment boundaries. The motion artifacts can include, for example, artifacts in the imaging of contrast agents used to enhance the visibility of blood or particular tissue types, or artifacts in imaging of blood flow, for example, ultrasound color flow or angio artifacts.

In one embodiment, the anatomical imaging includes one or more of ultrasound, magnetic resonance (MR), and CT imaging. In the embodiment wherein the anatomical imaging includes ultrasound imaging, the method further comprises completing the ultrasound imaging of a given volume size in less than ten (10) seconds.

Still further, acquiring image data representative of a first volume segment can include a first sequence of scan lines and acquiring image data representative of a second volume segment can include a second sequence of scan lines, wherein the first and second sequences of scan lines can include one of the following: a) a reverse acquisition order between the first sequence and second sequence of scan lines configured to provide a cross-boundary time alignment between adjacent volume segments, b) a boundary-to-center acquisition order configured to provide a cross-boundary time alignment between adjacent volume segments, or c) a center-to-boundary acquisition order configured to provide a cross-boundary time alignment between adjacent volume segments.

According to another embodiment, acquiring image data representative of a volume segment includes scanning the volume segment in a direction so that boundary sides of subvolumes of the volume segments are acquired at approximately the same exact phase of the physiological cycle when the anatomical feature is in the same position during a single physiological cycle of the subject. Still further, acquiring image data can comprise synchronizing acquisition of the image data to a selected phase of the subject's physiological cycle. Synchronizing acquisition of the image data can include cardiac gating and/or respiratory gating.

According to another embodiment, acquiring image data includes acquiring image data for interleaved volume segments in synchronism with successive physiological cycles of the subject. The method further includes displaying the three-dimensional anatomical image following completion of acquiring image data for the interleaved volume segments.

Figure 12:
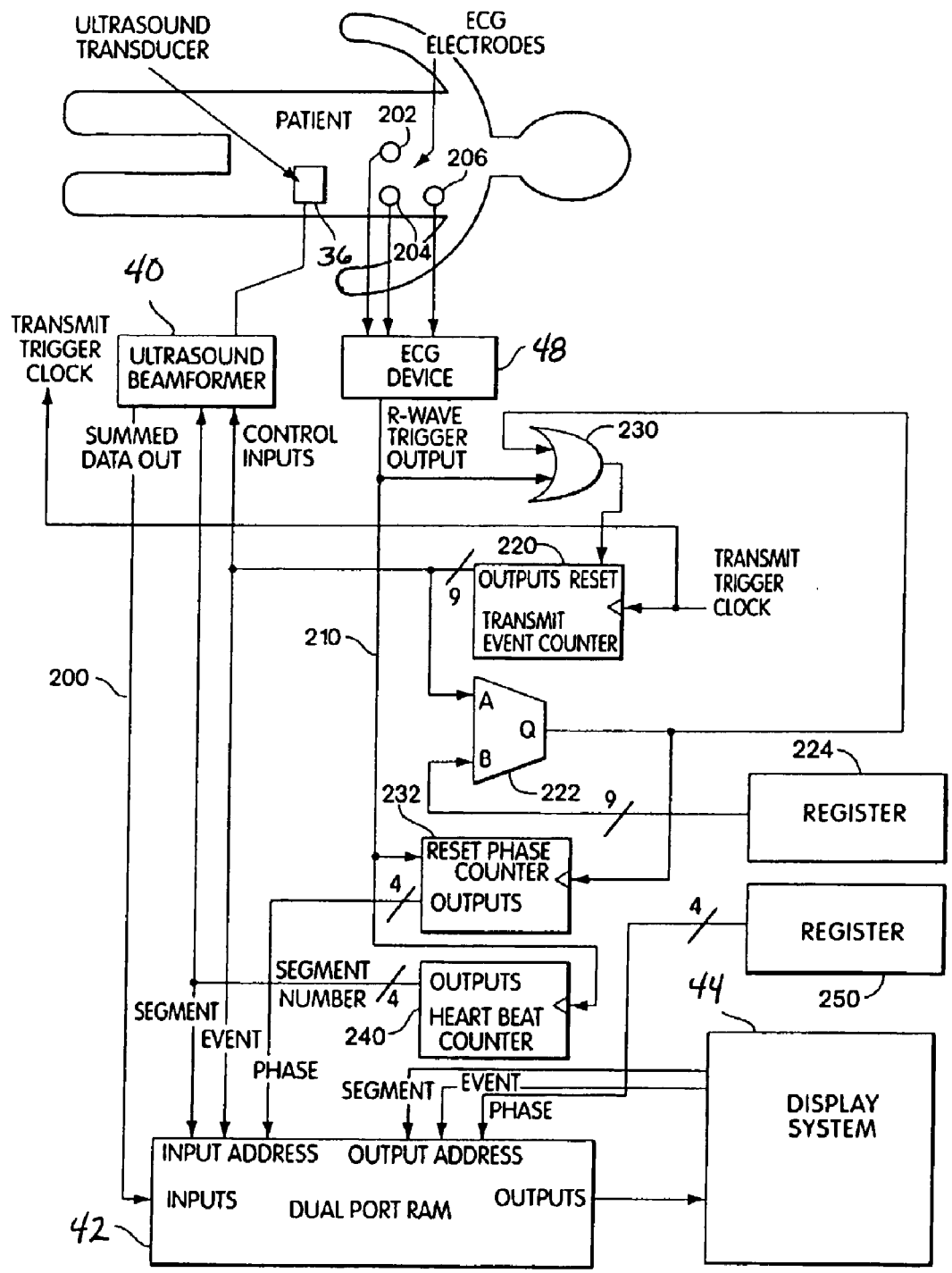
FIG. 12 is a schematic block diagram of an example of a system for cardiac ultrasound imaging in accordance with the invention.

A simplified block diagram of an example of a system for implementing segmented, three-dimensional cardiac imaging in accordance with the present embodiments is shown in FIG. 12. Like elements in FIGS. 3 and 12, have the same reference numerals. Ultrasound energy is transmitted into the region of interest in the patient by transducer array 36. Transmitter 32, T/R switch 34 and receiver 38 are omitted from FIG. 12 for ease of understanding. The received ultrasound echoes are processed by beamformer 40 to provide image data on line 200. The image data are stored in image data buffer 42, which in the example of FIG. 12 is a dual port random access memory (RAM).

ECG electrodes 202, 204 and 206, attached to the patient, sense the patient's cardiac cycle and provide signals to ECG device 48. The ECG device 48 provide an R-wave trigger output on line 210. The R-wave trigger output corresponds to the ECG waveform shown in FIG. 5.

A transmit trigger clock, which provides one pulse for each transmit event, is supplied to a transmit event counter 220 and to transmitter 32 (FIG. 3). The outputs of transmit event counter 220 are supplied to beamformer 40, to an event input address of image data buffer 42 and to a first input of a comparator 222. A register 224 stores the number of transmit events per cardiac phase. The outputs of register 224 are supplied to a second input of comparator 222. The output of comparator 222 is asserted when transmit event counter 220 reaches a count equal to the value stored in register 224. Thus, the output of comparator 222 is asserted when the required number of transmit events has been reached in each cardiac phase. The output of comparator is supplied to a first input of OR gate 230 and to the clock input of a cardiac phase counter 232. The outputs of phase counter 232, which indicate the cardiac phase for which image data is being acquired, are supplied to a phase input address of image data buffer 42.

The R-wave trigger output of ECG device 48 is supplied to a second input of OR gate 230, to the reset input of phase counter 232 and to the clock input of a heartbeat counter 240. The heartbeat counter 240 is incremented by the patient's heartbeats. The outputs of heartbeat counter 240 are supplied to a segment input address of image data buffer 42 and indicate the volume segment for which image data is being acquired. Thus, the input address of image data buffer 42 is made up of a segment input address which indicates volume segment, a phase input address which indicates cardiac phase and an event input address which indicates the transmit event within a specific volume segment and cardiac phase. The dual port RAM of image data buffer 42 may have locations for storage of image data corresponding to each transmit event of each volume segment of the image volume and corresponding to each phase of the patient's cardiac cycle.

The OR gate 230 supplies an output to the reset input of transmit event counter 220. Thus, transmit event counter is reset by the patient's heartbeat or when the comparator 222 indicates that the required number of transmit events has been completed for the current cardiac phase.

The output from image data buffer 42 is controlled by display system 44. Image data buffer 42 receives an output address, including a segment output address and an event output address from display system 44, and a cardiac phase output address from a register 250. Register 250 contains a value that indicates the cardiac phase to be displayed. The display system 44 combines the image data for the volume segments of the selected cardiac phase to produce a three-dimensional image of the image volume. By incrementing the value in register 250, three-dimensional images of different cardiac phases may be displayed in sequence. By incrementing to successive images at a suitable rate, images of heart movement may be displayed.

The control components of the imaging system of FIG. 12, including transmit event counter 220, comparator 222, OR gate 230, phase counter 232, heartbeat counter 240 and registers 224 and 250, may constitute part of system controller 46 (FIG. 3). It will be understood that the functions performed by these control components may be performed by a programmed microcomputer within the scope of the invention.

Figure 13:
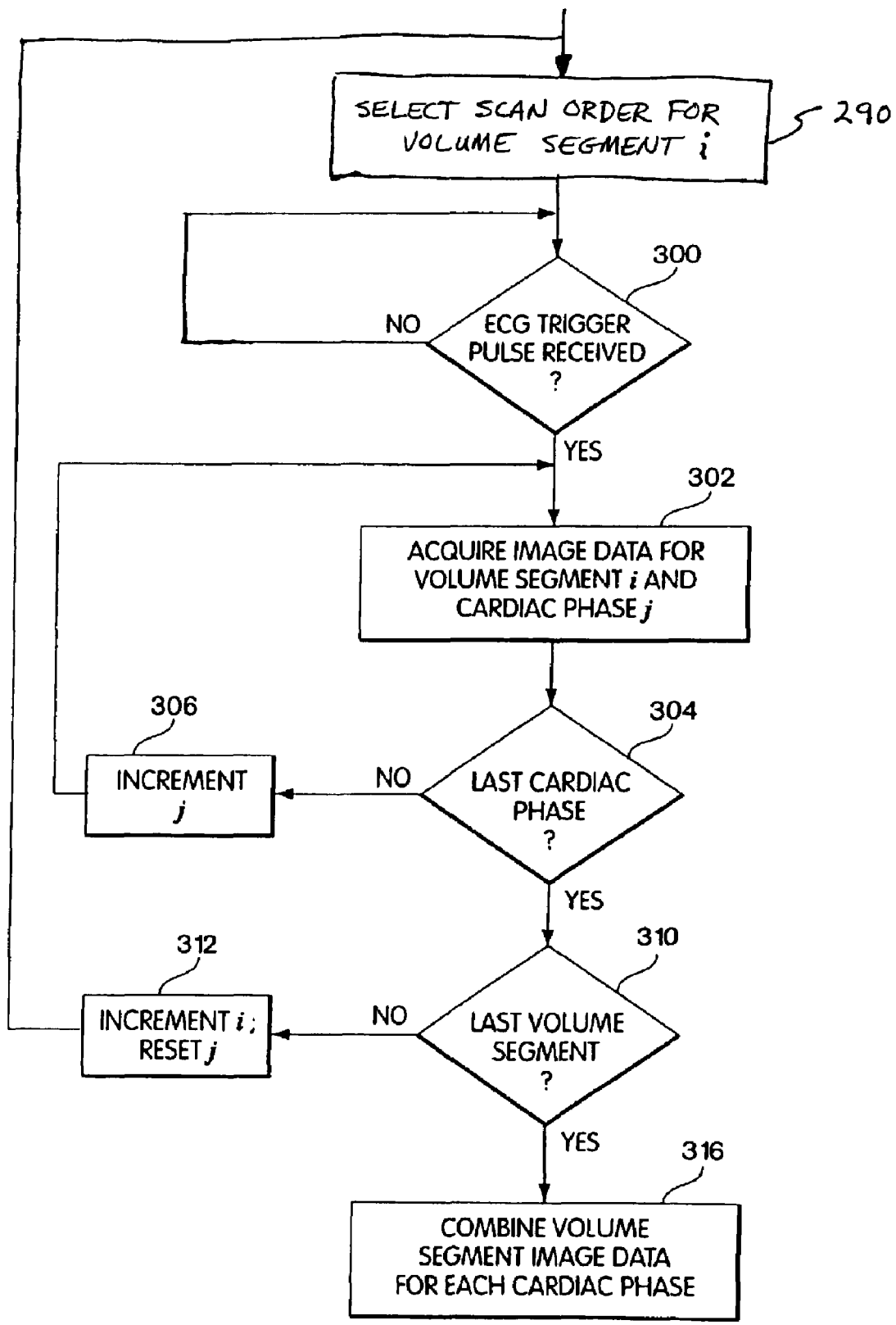
FIG. 13 is a flow diagram of an example of a method for cardiac ultrasound imaging in accordance with the invention.

A flowchart of a process for segmented three-dimensional cardiac imaging in accordance with one embodiment of the present disclosure is shown in FIG. 13. The process begins at step 290 with selection of the scan order for segment i. When an ECG trigger pulse is received, as determined in step 300, image data is acquired for volume segment i and cardiac phase j in step 302. The data acquisition step 302 involves generation of the specified number of transmit events for the volume segment, processing the received signals in beamformer 20 to provide image data and storing the image data in image data buffer 28. In step 304, a determination is made as to whether the current cardiac phase is the last cardiac phase in the cardiac cycle. When the current cardiac phase is not the last cardiac phase, a cardiac phase index j is incremented in step 306, and the process returns to step 302 for acquisition of image data for the next cardiac phase of the same cardiac cycle. When the current cardiac phase is the last cardiac phase, a determination is made in step 310 as to whether image data has been acquired for the last volume segment of the image volume. When the current volume segment is not the last volume segment, a volume segment index i is incremented and the cardiac phase index j is reset in step 312. The process then returns to step 290 for selection of the scan order for next volume segment i and then to step 300 to wait for the next ECG trigger pulse.

The process of FIG. 13 performs image data acquisition for one or more volume segments during each phase of the patient's cardiac cycle. Complete three-dimensional images of each cardiac phase are acquired in a relatively small number of heartbeats. When image data for all volume segments of the image volume has been acquired, the volume segment image data is combined in step 316 to provide a composite image for each of the cardiac phases.

The combining step involves combining image data for the volume segments of the image volume in the respective cardiac phases.

The embodiments of the present disclosure have been described in connection with acquisition of image data using a digital beamformer. It will be understood that the embodiments may be applied to analog implementations of ultrasound imaging systems.

Although only a few exemplary embodiments have been described in detail above, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

What is claimed is:

1. A computer implemented method for anatomical imaging, comprising:
   a) acquiring image data representative of three-dimensional, individually-continuous volume segments of an image volume of interest in a subject, in synchronism with corresponding physiological cycles of the subject, each of the volume segments containing image data distributed in three dimensions, wherein, for a pair of spatially consecutive ones of said volume segments, respective sequences of scan lines traversing said ones, said acquiring pair-wise mirror-images said sequences to minimize an occurrence of motion artifacts throughout the image volume; and
   b) combining the image data representative of the volume segments to produce a representation of a three-dimensional anatomical image of the image volume.

2. The method of claim 1, wherein acquiring image data further includes selecting the sequence of scan lines within each respective volume segment to minimize the occurrence of motion artifacts across adjacent volume segment boundaries.

3. The method of claim 1, wherein the motion artifacts include one selected from the group consisting of color flow and angio artifacts.

4. The method of claim 1, wherein the anatomical imaging includes one selected from the group consisting of ultrasound, magnetic resonance (MR), and CT imaging.

5. The method of claim 4, wherein the anatomical imaging includes ultrasound imaging, said method further comprising: completing the ultrasound imaging of a given volume size in less than ten (10) seconds.

6. The method of claim 1, further comprising:
   repeating said acquiring and said combining to generate a sequence of images; and
   forming one of the following selected from the group consisting of a time history of images and a motion picture of images.

7. The method of claim 1, wherein acquiring image data further includes configuring the sequence of scan lines within each respective volume segment to minimize time discontinuities within each volume segment, in addition to minimizing time discontinuities across adjacent volume segment boundaries.

8. The method of claim 1, wherein acquiring image data further includes configuring individual scan lines of a sequence to reduce a local time gradient throughout the volume segment to less than ten percent (10%) of a total time for acquiring image data for each volume segment.

9. The method of claim 1, wherein boundary sides of said ones of the volume segments are acquired at approximately the same exact phase of the physiological cycle when the anatomical feature is in the same position during a single physiological cycle of the subject.

10. The method of claim 1, wherein acquiring image data comprises synchronizing acquisition of the image data to a selected phase of the subject's physiological cycle, and synchronizing acquisition of the image data includes one selected from the group consisting of cardiac gating and respiratory gating.

11. A system for anatomical imaging, comprising:
an acquisition unit configured for acquiring image data representative of three-dimensional, individually-continuous volume segments of an image volume of interest in a subject, in synchronism with corresponding physiological cycles of the subject, each of the volume segments containing image data distributed in three dimensions, wherein, for a pair of spatially consecutive ones of said volume segments, respective sequences of scan lines traversing said ones, said acquiring pair-wise mirror-images said sequences to minimize an occurrence of motion artifacts throughout the image volume; and
a controller configured for combining the image data representative of the volume segments to produce a representation of a three-dimensional anatomical image of the image volume.

12. The system of claim 11, wherein said acquisition unit is configured to select the sequence of scan lines within each respective volume segment to minimize the occurrence of motion artifacts across adjacent volume segment boundaries, wherein the motion artifacts include one selected from the group consisting of color flow and angio artifacts.

13. The system of claim 11, wherein the anatomical imaging includes one selected from the group consisting of ultrasound, magnetic resonance (MR), and CT imaging.

14. The system of claim 13, wherein the anatomical imaging includes ultrasound imaging, wherein said controller is further configured for completing the ultrasound imaging of a given volume size in less than ten (10) seconds.

15. The system of claim 11, wherein said acquisition unit and controller repeat the acquiring and the combining to generate a sequence of images; and wherein said controller is further for forming one of the following selected from the group consisting of a time history of images and a motion picture of images.

16. The system of claim 11, wherein acquiring image data further includes configuring the sequence of scan lines within each respective volume segment to minimize time discontinuities within each volume segment in addition to minimizing time discontinuities across adjacent volume segment boundaries.

17. The system of claim 11, wherein acquiring image data further includes configuring individual scan lines of a sequence to reduce a local time gradient throughout the volume segment to less than ten percent (10%) of a total time for acquiring image data for each volume segment.

18. The system of claim 11, wherein boundary sides of said ones of the volume segments are acquired at approximately the same exact phase of the physiological cycle when the anatomical feature is in the same position during a single physiological cycle of the subject.

19. The system of claim 11, wherein said physiological cycles are successive.

20. A computer implemented method for anatomical imaging, comprising:
a) acquiring image data representative of three-dimensional volume segments of an image volume of interest in a subject, in synchronism with corresponding physiological cycles of the subject, each of the volume segments containing image data distributed in three dimensions, wherein acquiring image data includes selecting a sequence of scan lines for each respective volume segment configured to minimize an occurrence of mod on artifacts throughout the image volume; and
b) combining the image data representative of the volume segments to produce a representation of a three-dimensional anatomical image of the image volume, wherein acquiring image data representative of a first volume segment includes a first sequence of scan lines and acquiring image data representative of a second volume segment includes a second sequence of scan lines, said computer implemented method further comprising selecting the first and second sequences of scan lines from the group consisting of:
a) a reverse acquisition order between the first sequence and second sequence of scan lines configured to provide a cross-boundary time alignment between adjacent volume segments,
b) a boundary-to-center acquisition order configured to provide a cross-boundary time alignment between adjacent volume segments, and
c) a center-to-boundary acquisition order configured to provide a cross-boundary time alignment between adjacent volume segments.

21. A system for anatomical imaging, comprising:
an acquisition unit for acquiring image data representative of three-dimensional volume segments of an image volume of interest in a subject, in synchronism with corresponding physiological cycles of the subject, each of the volume segments containing image data distributed in three dimensions, wherein acquiring image data includes selecting a sequence of scan lines for each respective volume segment configured to minimize an occurrence of motion artifacts throughout the image volume; and
a controller for combining the image data representative of the volume segments to produce a representation of a three-dimensional anatomical image of the image volume, wherein acquiring image data representative of a first volume segment includes a first sequence of scan lines and acquiring image data representative of a second volume segment includes a second sequence of scan lines, wherein the first and second sequences of scan lines is selected from the group consisting of:
a) a reverse acquisition order between the first sequence and second sequence of scan lines configured to provide a cross-boundary time alignment between adjacent volume segments,
b) a boundary-to-center acquisition order configured to provide a cross-boundary time alignment between adjacent volume segments, and
c) a center-to-boundary acquisition order configured to provide a cross-boundary time alignment between adjacent volume segments.

22. Apparatus for medical ultrasound imaging, comprising:
a transducer comprising an array of transducer elements;
a transmitter for transmitting ultrasound energy with said transducer into an image volume of interest in a subject's body as a plurality of transmit beams;

a receiver for receiving ultrasound echoes with said transducer from the image volume in response to the ultrasound energy and for generating received signals representative of the received ultrasound echoes;

a receive beamformer for processing the received signals to form at least one receive beam for each of the transmit beams and to generate image data representative of the ultrasound echos in the receive beam;

a device coupled tote subject for generating a signal representative of a physiological cycle of the subject;

a controller responsive to the physiological signal for controlling said transmitter and said receive beamformer to acquire image data representative of three-dimensional, individually-continuous volume segments of the image volume in synchronism with corresponding physiological cycles of the subject, each of the volume segments containing image data distributed in three dimensions, wherein, for a pair of spatially-consecutive ones of said volume segments, respective sequences of scan lines traversing said ones, said acquiring pair-wise mirror-images said sequences to minimize an occurrence of motion artifacts throughout the image volume; and a circuit for combining the image data representative of the volume segments to produce a representation of a three-dimensional ultrasound image of the image volume.

23. The apparatus of claim 22, wherein said transducer includes a two-dimensional array of transducer elements.

24. The apparatus of claim 22, wherein said controller further includes means for synchronizing acquisition of the image data to a selected phase of the subject's physiological cycle.

25. The apparatus of claim 22, wherein said controller further includes means for defining multiple physiological phases of the subject's physiological cycle, means for acquiring image data for a three-dimensional volume segment during each of the physiological phases of a physiological cycle, and means for repeating the data acquisition for different ones of the three-dimensional volume segments during different physiological cycles.

26. The apparatus of claim 25, wherein said combining circuit includes means for combining the volume segment image data for respective physiological phases to provide three-dimensional ultrasound images representative of each of the physiological, phases.

27. The apparatus of claim 25, wherein said controller includes means for acquiring image data for abutting volume segments in synchronism with successive physiological cycles of the subject.

28. A computer implemented method for anatomical imaging, comprising:
a) acquiring image data representative of three-dimensional, mutually-interleaved volume segments of an image volume of interest in a subject, in synchronism with corresponding physiological cycles of the subject each of the volume segments containing image data distributed in three dimensions, wherein acquiring image data includes selecting a sequence of scan lines for each respective volume segment tat traverses said volume segment, said selecting being performed such tat said sequences are spatially staggered within said image volume, said acquiring being configured to minimize an occurrence of motion artifacts throughout the image volume; and
b) combining the image data representative of the volume segments to produce a representation of a three-dimensional anatomical image of the image volume.

29. A system for anatomical imaging, comprising:

an acquisition unit configured for said acquiring of claim 28; and a controller configured for said combining of claim 28.

30. The method of claim 28, wherein said cycles are successive.

31. The method of claim 28, further comprising displaying a low resolution image of the image volume during image data acquisition.

* * * * *